(12) United States Patent
Keum et al.

(10) Patent No.: US 10,190,120 B2
(45) Date of Patent: Jan. 29, 2019

(54) ZN-DPA COMPLEX COMPOUNDS AND SIRNA DELIVERY SYSTEMS CONTAINING THE SAME

(71) Applicant: KOREA INSTITUTE OF SCIENCE AND TECHNOLOGY, Seoul (KR)

(72) Inventors: Gyo Chang Keum, Seoul (KR); Eun Kyoung Bang, Seoul (KR); Jin Bum Kim, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 0 days.

(21) Appl. No.: 15/671,901

(22) Filed: Aug. 8, 2017

(65) Prior Publication Data

US 2018/0044674 A1 Feb. 15, 2018

(30) Foreign Application Priority Data

Aug. 9, 2016 (KR) .................. 10-2016-0101150

(51) Int. Cl.
*C07F 3/06* (2006.01)
*C07D 401/12* (2006.01)
*A61K 48/00* (2006.01)
*C12N 15/113* (2010.01)
*C07D 213/38* (2006.01)
*C07D 495/04* (2006.01)
*C12N 15/11* (2006.01)

(52) U.S. Cl.
CPC .......... *C12N 15/113* (2013.01); *C07D 213/38* (2013.01); *C07D 495/04* (2013.01); *C07F 3/06* (2013.01); *C12N 15/111* (2013.01); *C12N 2310/14* (2013.01); *C12N 2320/32* (2013.01); *C12N 2320/51* (2013.01)

(58) Field of Classification Search
CPC .... A61K 47/18; A61K 48/00; A61K 48/0008; C12N 15/14; C12N 15/32; C12N 15/111; C12N 15/113
USPC ....... 435/6.1, 91.1, 91.31, 455, 458; 514/44; 536/23.1, 24.5
See application file for complete search history.

(56) References Cited

U.S. PATENT DOCUMENTS

2009/0233373 A1 9/2009 Hamachi et al.
2014/0162966 A1 6/2014 Chen et al.

OTHER PUBLICATIONS

Kim et al (Bioconjugate Chemistry, vol. 27, pp. 1850-1856 (Jun. 30, 2016)) (Year: 2016).*
"Toward Cellular Uptake: Poly(disulfide)s and Pseudo Amphiphiles", Oct. 14, 2015, Total of 2 pages.
"Tunable siRNA Transporters with a Zinc(II)-Dipicolylamine Complex as the Head", Apr. 20, 2016, Total of 2 pages.
Choi et al., "A nanoparticle formula for delivering siRNA or miRNAs to tumor cells in cell culture and in vivo", Nature Protocols, vol. 9, No. 8, 2014, pp. 1900-1915.
Choi et al., "Versatile RNA Interference Nanoplatform for Systemic Delivery of RNAs", American Chemical Society, vol. 8, No. 5, 2014, pp. 4559-4570.
Jiang et al., "Dynamic molecular recognition on the surface of vesicle membranes", Chem. Commun., 2006, pp. 1407-1409.
Kim et al., "Coordinative Amphiphiles as Tunable siRNA Transporters", Bioconjugate Chemistry, Jun. 30, 2016, Total of 8 pages.
Kim et al., "Pseudo Amphiphiles as Novel siRNA Transporters", AIMECS 2015, Oct. 18, 2015, Total of 2 pages.
Kohira et al., "Artificial Receptors Designed for Intracellular Delivery of Anionic Phosphate Derivatives", ChemBioChem 2008, vol. 9, pp. 698-701.
Liu et al., "Sticky Nanoparticles: A Platform for siRNA Delivery by a Bis(zinc(II)dipicolylamine)-Functionalized, Self-Assembled Nanoconjugate", Angew. Chem. Int. Ed. 2012, 51, pp. 445-449.

* cited by examiner

*Primary Examiner* — Jane J Zara
(74) *Attorney, Agent, or Firm* — Birch, Stewart, Kolasch & Birch, LLP

(57) ABSTRACT

Provided herein are a novel Zn-DPA complex compound and an siRNA delivery system including the same as a transporter, the Zn-DPA complex compound including: a phosphate-directing functional part of zinc (II)-dipicolylamine ("Zn-DPA"); a cell membrane-directing functional part; and a linker part that links the phosphate-directing functional part and the cell membrane-directing functional part. The Zn-DPA complex compound has low toxicity and efficiently delivers siRNA to cells, thereby useful in various ways for various studies and diagnosis and treatment of diseases, which use siRNA.

11 Claims, 6 Drawing Sheets

ZN-DPA COMPLEX COMPOUNDS AND SIRNA DELIVERY SYSTEMS CONTAINING THE SAME

CROSS-REFERENCE TO RELATED APPLICATION

This application claims under 35 U.S.C. § 119(a) the benefit of Korean Patent Application No. 10-2016-0101150 filed on Aug. 9, 2016, the entire contents of which are incorporated herein by reference.

BACKGROUND

(a) Technical Field

The present disclosure relates to a novel Zn-DPA complex compound and an siRNA delivery system including the same as a transporter. The Zn-DPA complex compound being composed of a phosphate-directing functional part of zinc (II)-dipicolylamine (hereinafter, referred to as "Zn-DPA"), a cell membrane-philic functional part, and a linker part that links the phosphate-directing functional part and the cell membrane-directing functional part.

(b) Background Art

The RNA interference technology has been reported as the most powerful and efficient method among genetic therapies known until now. A small interfering RNA (hereinafter, referred to as siRNA) is a double-stranded RNA composed of 15 to 30 nucleotides. The siRNA suppresses the expression of a gene by specifically cleaving only an mRNA having a base sequence that is the same as that of the siRNA, and is a therapeutic agent for treating various diseases such as cancer, hereditary disease, and virus infection by using these siRNA characteristics, and studies on the siRNA have been actively conducted.

However, there are problems in that the siRNA may be easily cleaved by various RNases in the organism due to low stability of the siRNA, and the siRNA may not easily pass through their cell membrane due to the anionic properties. Thus, there is a need for developing a new siRNA transporter which achieves high therapeutic efficiency by safely delivering the siRNA to a target cell.

The siRNA transporter is largely classified into viral and non-viral transporters. The viral transporter is advantageous in high delivery efficiency thereof in cells, but since the discovery of toxicity problems in the clinical stage, recent studies have been focused on the non-viral transporters. As the non-viral transporter used to deliver the siRNA, cationic materials such as cationic liposomes, chitosan nanoparticles, and polyethylenimine nanoparticles are known. Among the aforementioned non-viral transporters, the cationic liposome is an amphiphilic molecule composed of a cationic head and a hydrophobic tail, and resembles a lipid molecule of the cell membrane, and it is known that the cationic head part is bonded to a phosphoric acid skeleton of siRNA, which exhibits negative charges through electrostatic attraction force to form hard nano-sized particles. However, cationic materials used as an siRNA transporter are also responsible for toxicity caused by non-specific bonds with various proteins present in the blood vessel when the cationic materials are introduced into the organism. As a method to solve the problems, the cationic liposome is also used while being modified with ethylene glycol, and the like.

In the present invention, studies and efforts have been made to develop a new siRNA transporter which is capable of reducing toxicity while maintaining the interaction with siRNA.

The above information disclosed in this Background section is only for enhancement of understanding of the background of the invention and therefore it may contain information that does not form the conventional art that is already known in this country to a person of ordinary skill in the art.

SUMMARY OF THE DISCLOSURE

The present invention has been made in an effort to solve the above-described problems associated with conventional art.

The present invention has been made in an effort to provide a novel dipicolylamine-based compound that is useful as a ligand that forms complexes with zinc metal ions ($Zn^{2+}$).

The present invention has been made in an effort to provide a novel zinc complex compound in which zinc metal ions ($Zn^{2+}$) and the aforementioned dipicolylamine-based compound form complex bonds.

The present invention has been made in an effort to provide a use in which the aforementioned zinc complex compound is used as an siRNA transporter.

The present invention has been made in an effort to provide an siRNA delivery system including: siRNA; and the aforementioned zinc complex compound as a transporter.

In one aspect, the present invention provides a dipicolylamine-based compound represented by the following Formula 1.

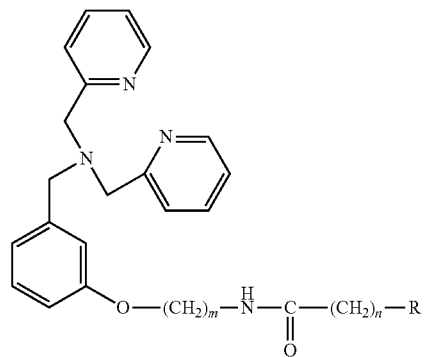

[Formula 1]

in Formula 1,
R represents a monocyclic or fused cyclic aliphatic heterocyclic group including 1 to 5 heteroatoms selected from the group consisting of a saturated or unsaturated linear aliphatic hydrocarbon group having 5 to 15 carbon atoms; an aromatic hydrocarbon group having 6 to 16 carbon atoms; or a nitrogen atom (N), a sulfur atom (S) and an oxygen atom (O), and the aliphatic heterocyclic group may or may not include an oxo (=O) group, and
m represents an integer from 1 to 10 and n represents an integer from 0 to 10.

In the present invention, 'a linear aliphatic hydrocarbon group' may have 5 to 15 carbon atoms linked in a straight or branched chain. Further, the linear aliphatic hydrocarbon group may be a saturated hydrocarbon group in which the carbon atoms are linked through a single bond, or an unsaturated linear hydrocarbon group including 1 to 5 double bonds or triple bonds. For example, the saturated linear aliphatic hydrocarbon group may include a pentyl group, a hexyl group, a heptyl group, an octyl group, a nonyl group, a decyl group, an undecyl group, a dodecyl group, a tridecyl group, a tetradecyl group, a pentadecyl group, or a structural isomer thereof. The unsaturated linear aliphatic hydrocarbon group may include a 1-pentenyl group, a 2-pentenyl group, a 1,2-pentadienyl group, a 1-hexenyl group, a 2-hexenyl group, a 1,3-hexadienyl group, a 1-heptenyl group, a 2-heptenyl group, a 3-heptenyl group, a 1-octenyl group, a 2-octenyl group, a 3-octenyl group, a 1-nonenyl group, a 2-nonenyl group, a 3-nonenyl group, a 1-decenyl group, a 2-decenyl group, a 3-decenyl group, an 1-undecenyl group, a 2-undecenyl group, a 3-undecenyl group, a 4-undecenyl group, a 5-undecenyl group, a 1-dodecenyl group, a 2-dodecenyl group, a 3-dodecenyl group, a 4-dodecenyl group, a 5-dodecenyl group, a 1-tridecenyl group, a 2-tridecenyl group, a 3-tridecenyl group, a 4-tridecenyl group, a 5-tridecenyl group, a 6-tridecenyl group, or a structural isomer thereof.

In the present invention, 'an aromatic hydrocarbon group' may be composed of a monocyclic, bicyclic, tricyclic, or tetracyclic ring, which includes 6 to 16 carbon atoms, or two or more rings may also form a fused ring. For example, the aromatic hydrocarbon group may include a phenyl group, a biphenyl group, a naphthyl group, an anthryl group, a phenanthryl group, a pyrenyl group, and the like.

In the present invention, 'an aliphatic heterocyclic group' may be a single ring or fused ring including 1 to 5 heteroatoms composed of a nitrogen atom (N), a sulfur atom (S), and an oxygen atom (O). Further, the aliphatic heterocyclic group may or may not include an oxo (=O) group. For example, the aliphatic heterocyclic group may include a tetrahydrothiophenyl group, an imidazolidinyl group, an imidazolidin-2-one group, tetrahydro-1H-thieno[3,4-d]imidazole, tetrahydro-1H-thieno[3,4-d]imidazol-2(3H)-one, and the like.

The dipicolylamine-based compound represented by Formula 1 may be preferably a dipicolylamine-based compound in which R represents a linear aliphatic hydrocarbon group having 2 to 10 carbon atoms and including 0 to 3 double bonds;

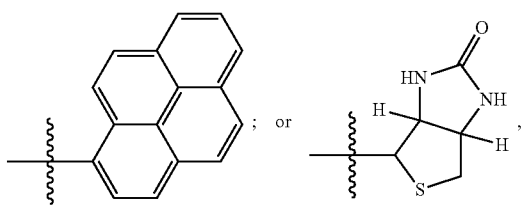 [SMILES: *c1ccc2ccc3cccc4ccc1c2c34 ; *C1SCC2NC(=O)NC21]

and m or n is each an integer from 3 to 8.

The dipicolylamine-based compound represented by Formula 1 may be more preferably represented by the following Formula 1a, 1b, or 1c.

[Formula 1a]

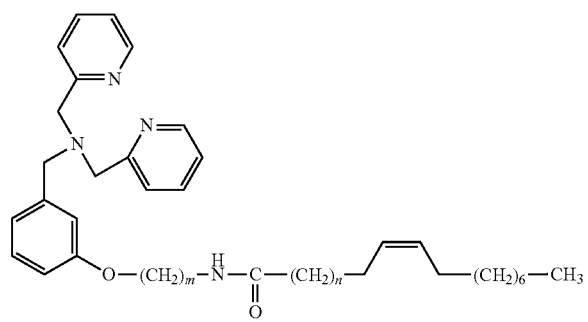

[Formula 1b]

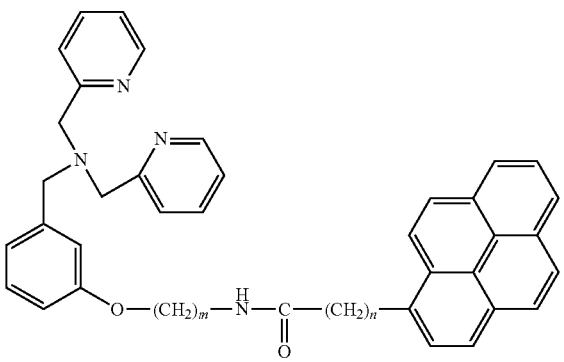

[Formula 1c]

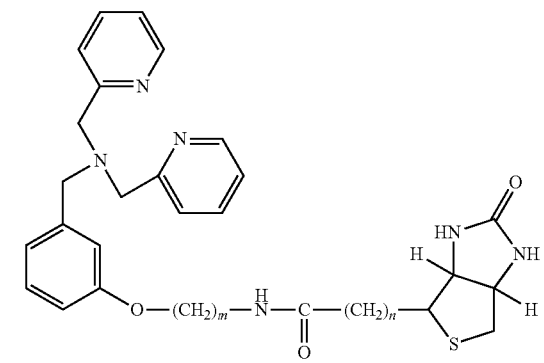

In Formula 1a, 1b, or 1c, m represents an integer from 1 to 10, and n represents an integer from 0 to 10.

In another aspect, the present invention provides a Zn-DPA complex compound in which zinc metal ions ($Zn^{2+}$) and the dipicolylamine-based compound represented by Formula 1 are complex-bonded.

The Zn-DPA complex compound of the present invention may be represented by the following Formula 2.

[Formula 2]

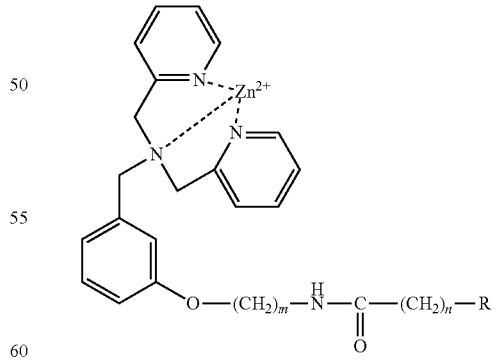

In Formula 2, R, m, and n are each the same as those defined in Formula 1.

The Zn-DPA complex compound represented by Formula 2 may be specifically represented by, for example, the following Formula 2a, 2b, or 2c.

[Formula 2a]

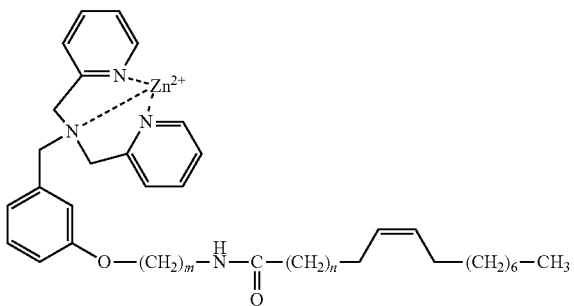

[Formula 2b]

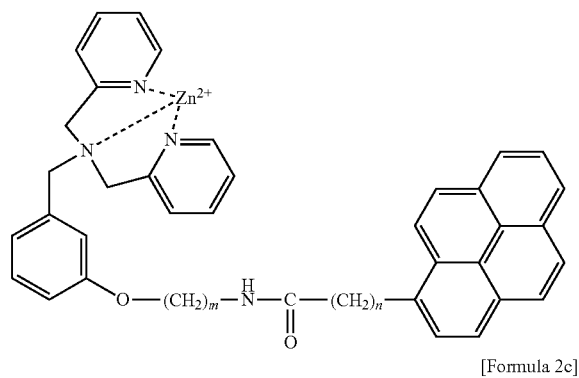

[Formula 2c]

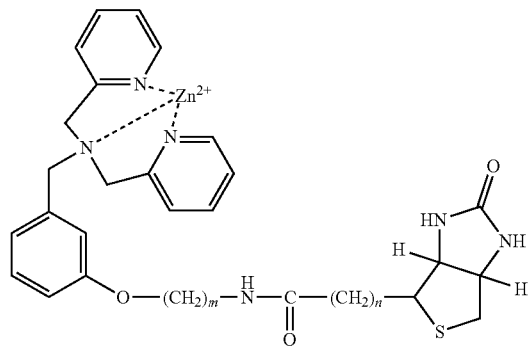

In Formula 2a, 2b, or 2c, m represents an integer from 1 to 10, and n represents an integer from 0 to 10.

In still another aspect, the present invention provides a use in which the Zn-DPA complex compound represented by Formula 2 is used as a siRNA transporter.

As illustrated in FIG. 1, the Zn-DPA complex compound of the present invention is composed of a phosphate-directing functional part (Constitution A), a cell membrane-directing functional part (Constitution C), and a linker part (Constitution B) that links the phosphate-directing functional part and the cell membrane-directing functional part. That is, the Zn-DPA complex compound of the present invention forms an amphiphilic unimolecular structure.

Considering that the Zn-DPA complex compound of the present invention is compared with a cationic liposome compound in the related art composed of cationic head part-linker part-hydrophobic tail part, it can be seen that the Zn-DPA complex compound of the present invention is different from the cationic liposome compound in the related art in that the complex compound is an amphiphilic unimolecular compound.

The structure of the Zn-DPA complex compound of the present invention will be specifically reviewed as follows.

The phosphate-directing functional part (Constitution A) has Zn-DPA introduced as a molecular group that specifically recognizes a phosphoric acid skeleton of siRNA. The Zn-DPA selected as a phosphoric acid group recognition site is specifically bonded to a phosphoric acid group of siRNA through a coordination bond. An ammonium cationic molecular group, which is applied to a typical phosphoric acid group recognition site, is bonded to a phosphoric acid group through electrostatic attraction force, whereas the Zn-DPA is characterized by being bonded to a phosphoric acid group of siRNA through a coordination bond. The Zn-DPA may dye the surface of cells by recognizing a phospholipid molecule of a cell membrane through a coordination bond, or may be applied to determining the activity of kinase by determining the degree of phosphorylation of protein.

The cell membrane-directing functional part (Constitution C) may be used without particular limitation as long as the cell membrane-directing functional part (Constitution C) is a compound having an end carboxylic acid group which has affinity for the cell membrane. Furthermore, when a compound capable of being selectively bonded to a specific tissue or disease cell is used as a cell membrane-directing functional part, the compound may also be applied as a targeted delivery system. The exemplary embodiment of the present invention representatively exemplifies an example in which a linear aliphatic hydrocarbon group derived from a fatty acid such as oleic acid known to be a constituent material of phospholipid as a cell membrane-directing functional part, an aromatic hydrocarbon group derived from 4-(pyrenyl)butanoic acid, and the like having excellent affinity for the cell membrane, and an aliphatic heterocyclic group such as biotin capable of being targeted as a ligand of a vitamin receptor overexpressed in cancer cells are introduced, but the cell membrane-directing functional part of the present invention is not limited to a partial group exemplified in the exemplary embodiment. The siRNA delivery mechanism may vary depending on the selection of the cell membrane-directing functional part, and the cell membrane-directing functional part may be diversely adjusted depending on the use purpose of siRNA. Accordingly, in addition to the cell membrane-directing functional part exemplified in exemplary embodiment of the present invention, any group may be used as a cell membrane-directing functional part without limitation as long as the group is an aliphatic linear hydrocarbon group, an aromatic hydrocarbon group, or an aliphatic heterocyclic group, which may be used for the same purpose.

The linker part (Constitution B) serves as a linker that links the phosphate-directing functional part and the cell membrane-directing functional part. In the present invention, a 3-(aminoalkoxy)benzyl group was used as a linker part that links the phosphate-directing functional part and the cell membrane-directing functional part. The 3-(aminoalkoxy)benzyl group is devised in consideration of characteristics of the phosphate-directing functional part and the cell membrane-directing functional part. That is, a benzyl group, which is easily bonded to a nitrogen atom (N) of the Zn-DPA phosphate-directing functional part, was introduced into one end of the linker part, and an amine group, which forms an amide bond with a carboxylic acid group of the cell membrane-directing functional part, was introduced into the other end. Further, it was possible to adjust the number (m) of carbon chains of the linker part so as to be suitable for the siRNA gene characteristics.

Accordingly, the Zn-DPA complex compound of the present invention is devised in consideration of siRNA and cell membrane-directing characteristics, and may be useful as an siRNA transporter because it is possible to target and deliver siRNA to a specific cell.

In a further aspect, the present invention provides an siRNA delivery system including: siRNA; and the Zn-DPA complex compound represented by Formula 2 as a transporter.

Specifically, provided is an siRNA delivery system including a composite in which siRNA and the Zn-DPA complex compound represented by Formula 2 as an siRNA transporter are bonded to each other at a molar ratio of 1:16 to 1,000, preferably 1:100 to 600. In the present invention, the Zn-DPA complex compound devised as a siRNA transporter is slightly toxic, and may efficiently deliver siRNA by enhancing the stability of siRNA for various cleavage enzymes present in the organism. That is, a composite formed by bonding siRNA and the Zn-DPA complex compound may suppress a target protein from being expressed by stably delivering siRNA to a target cell.

The siRNA transporter of the present invention exhibits excellent efficacy compared to Lipofectamine™ (Invitrogen) which is a commercially available cell permeation auxiliary agent in terms of toxicity and efficacy.

Further, in the siRNA transporter of the present invention, it is possible to achieve a cell delivery to some degree by using only the Zn-DPA phosphate-directing functional part (Constitution A), but when the cell membrane-directing functional part (Constitution C) is linked to the Zn-DPA phosphate-directing functional part (Constitution A), siRNA may be not only easily delivered, but also stably delivered to the target protein.

Accordingly, the siRNA transporter of the present invention may be applied to a genetic therapy to treat various diseases such as cancer, hereditary disease, and virus infection.

Other aspects and preferred embodiments of the invention are discussed infra.

It is understood that the term "vehicle" or "vehicular" or other similar term as used herein is inclusive of motor vehicles in general such as passenger automobiles including sports utility vehicles (SUV), buses, trucks, various commercial vehicles, watercraft including a variety of boats and ships, aircraft, and the like, and includes hybrid vehicles, electric vehicles, plug-in hybrid electric vehicles, hydrogen-powered vehicles and other alternative fuel vehicles (e.g. fuels derived from resources other than petroleum). As referred to herein, a hybrid vehicle is a vehicle that has two or more sources of power, for example both gasoline-powered and electric-powered vehicles.

The above and other features of the invention are discussed infra.

BRIEF DESCRIPTION OF THE DRAWINGS

The above and other features of the present invention will now be described in detail with reference to certain exemplary embodiments thereof illustrated in the accompanying drawings which are given hereinbelow by way of illustration only, and thus are not limitative of the present invention, and wherein.

The Zn-DPA complex compound of the present invention forms an amphiphilic structure in which a phosphate-directing functional part (Constitution A) and a cell membrane-directing functional part (Constitution C) are linked to each other through a linker part (Constitution B). The amphiphilic structure is roughly different from a cationic lipid compound in the related art.

Figure 1:
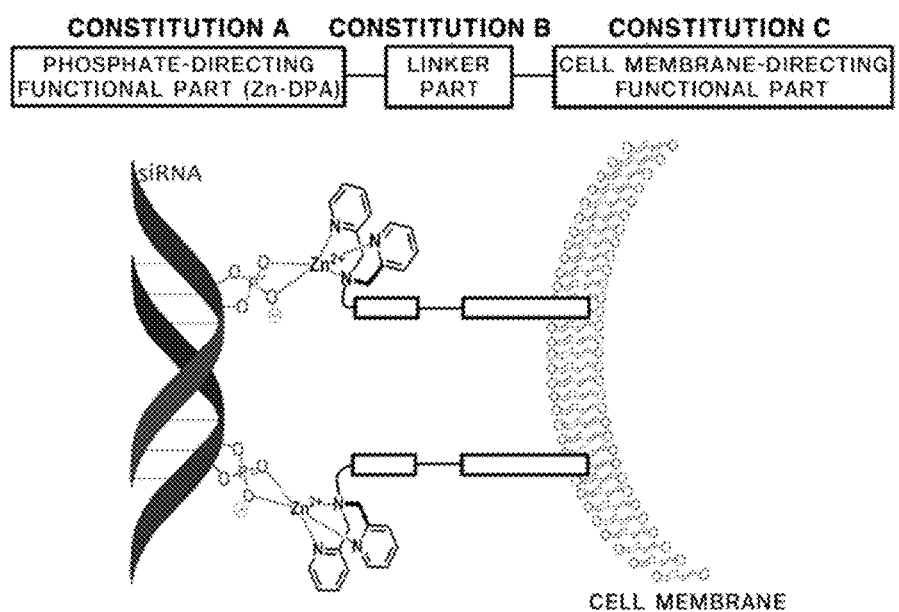
FIG. 1 is a schematic view illustrated by diagramming the overview of the present invention.
Figure 2:
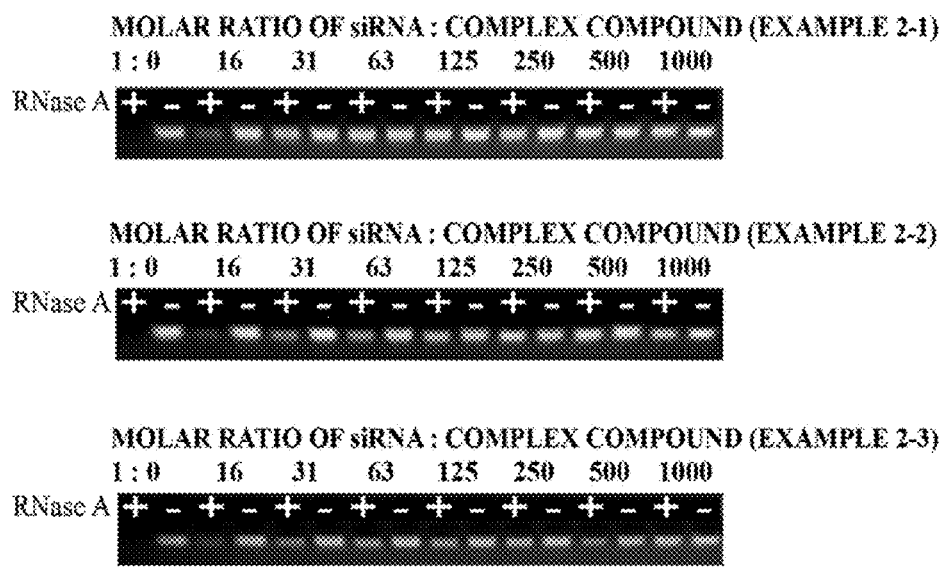

FIG. 2 illustrates a result of determining the stability of a composite, which the Zn-DPA complex compound and siRNA form, against a RNA hydrolase.

The composite of siRNA and the Zn-DPA complex compound had excellent stability against the RNA hydrolase. In terms of stability against the RNase A enzyme, the Zn-DPA complex compound synthesized in Example 2-1 was the best among the Zn-DPA complex compounds, and when the molar ratio of siRNA and the Zn-DPA complex compound was 1:63 or more, almost all the siRNA remained without being cleaved.

Figure 3:
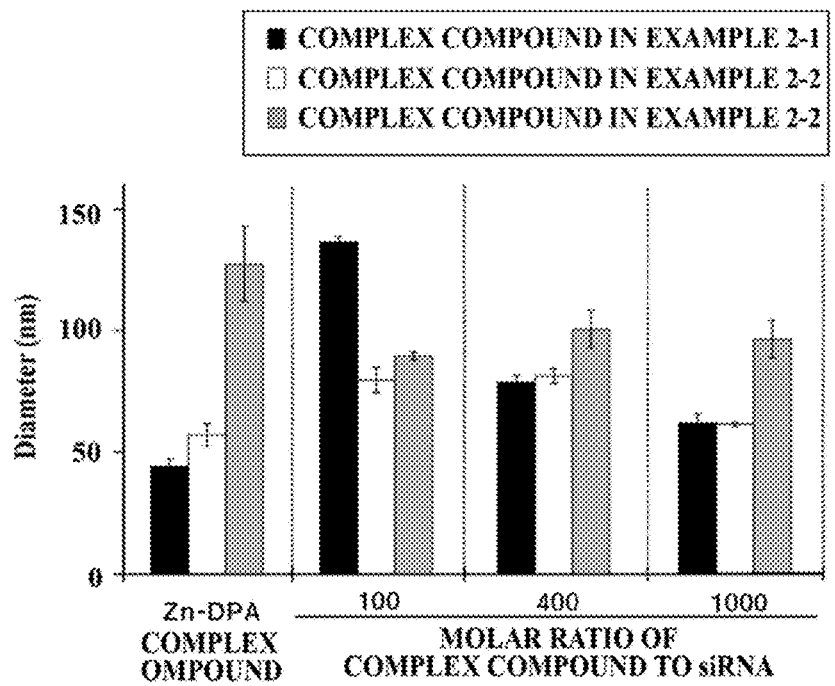

FIG. 3 shows a result of measuring the size of nanoparticles which the Zn-DPA complex compound and siRNA form.

The Zn-DPA complex compound against siRNA exhibited a size of about 100 nm, which corresponds to a size of 200 nm or less, which is known to be appropriate for the complex compound to pass through a cell membrane by endocytosis. When the results of FIGS. 2 and 3 are put together, the Zn-DPA complex compound forms nanoparticles having a size suitable for endocytosis through binding force to RNA and interaction between cell membranes, and exhibits excellent properties as an siRNA transporter because the Zn-DPA complex compound also provides stability against the RNA hydrolase.

Figure 4:
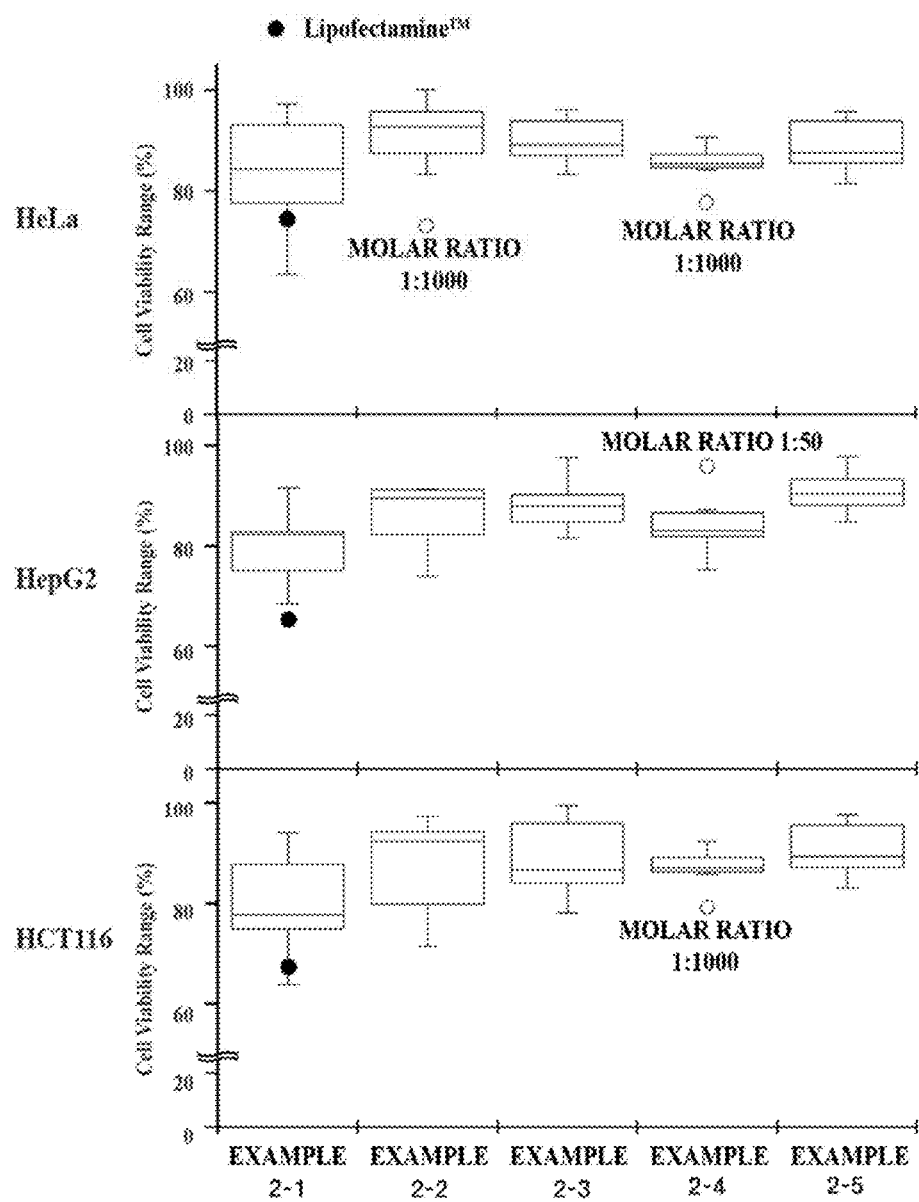

FIG. 4 is a graph showing a result of determining a cytotoxicity of the Zn-DPA complex compound.

When a molar ratio of siRNA and the Zn-DPA complex compound was within a range of 1:50 to 1,000, the Zn-DPA complex compound did not usually exhibit toxicity as compared to Lipofectamine™ (Invitrogen), which is a commercially available cell permeation auxiliary agent.

Figure 5:
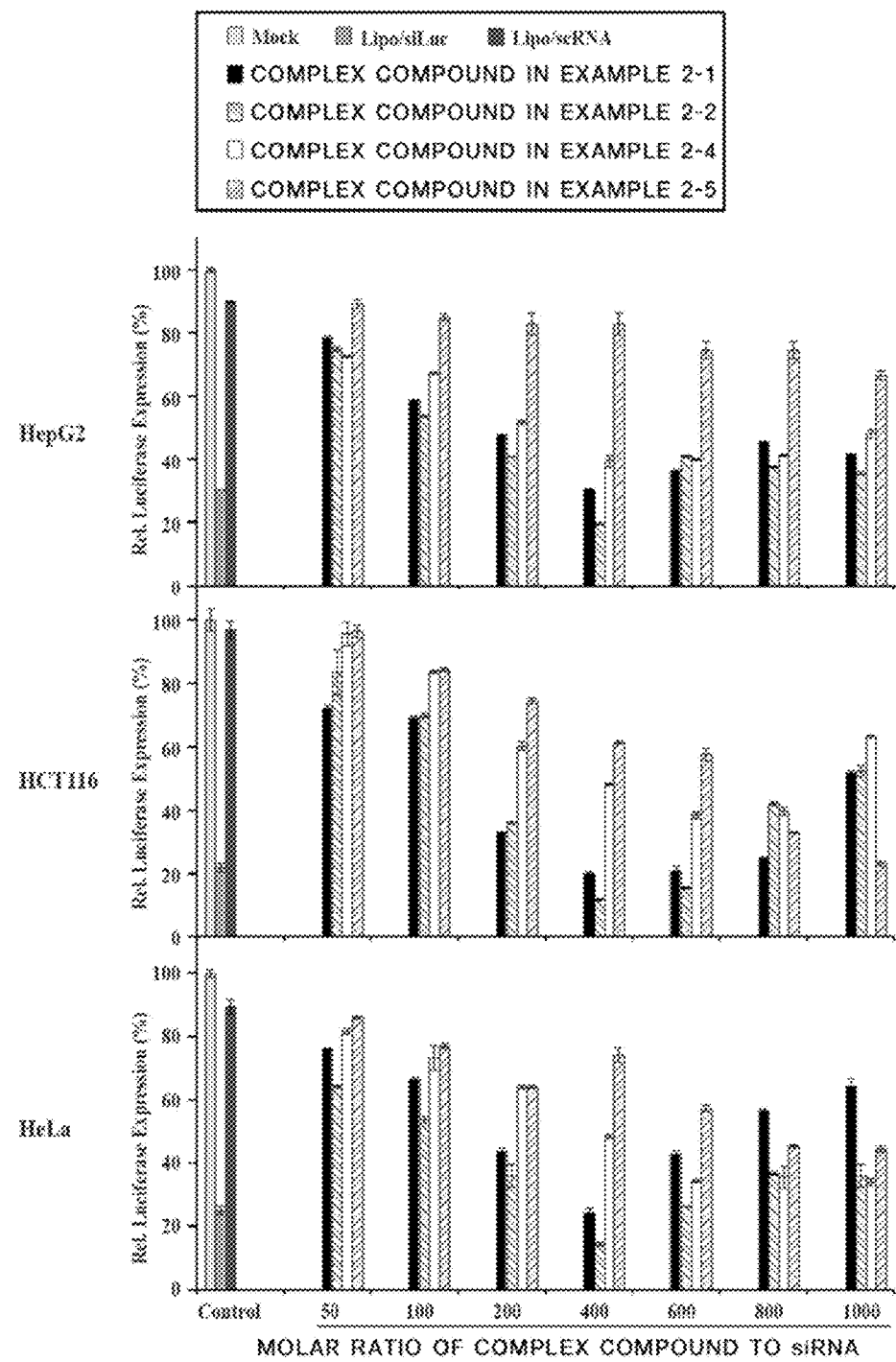

FIG. 5 is a graph showing a result of determining a cell delivery efficiency of the Zn-DPA complex compound.

The cell delivery efficiency was determined from a decreasing signal of fluorescence exhibited by treating the composite of siRNA and the Zn-DPA complex compound with HeLa, HCT116, and HepG2 cell lines and suppressing the luciferase from being expressed. It can be confirmed that the Zn-DPA complex compounds (compounds in Examples 2-4 and 2-5) including only Zn-DPA being a phosphoric acid functional part also exhibit a certain degree of cell delivery efficiency, but the Zn-DPA complex compounds (compounds in Examples 2-1 and 2-2), to which the cell membrane-directing functional part is linked, have a much more amplified cell delivery efficiency than the cell delivery efficiency. The Zn-DPA complex compound in Example 2-1 or 2-2 exhibited a much better cell delivery efficiency than that of Lipofectamine™ (Invitrogen), which is a commercially available cell permeation auxiliary agent. Further, when the molar ratio of siRNA and the Zn-DPA complex compound is 1:400, an optimal delivery efficiency was exhibited.

Figure 6:
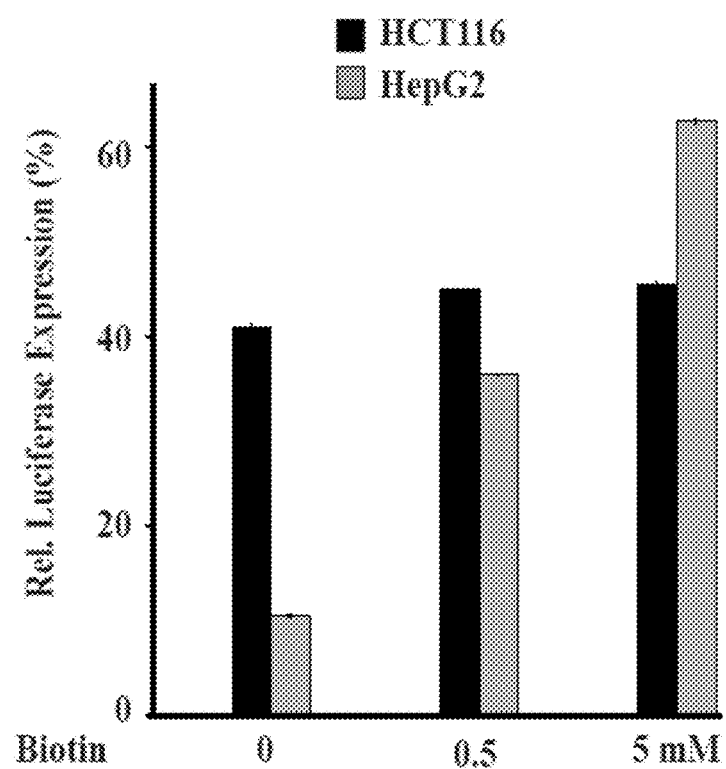

FIG. 6 is a graph illustrating a result that confirms an effect of biotin on the cell delivery efficiency of the Zn-DPA complex compound.

In the HepG2 cell line including a large amount of a biotin receptor, the cell delivery efficiency was dropped in competition with biotin, whereas in the HCT116 cell line including little biotin receptor, cells were not delivered well regardless of biotin. From the result, it can be seen that in the intracellular delivery of the Zn-DPA complex compound (compound in Example 2-3), the biotin receptor serves an important role.

Figure 7:
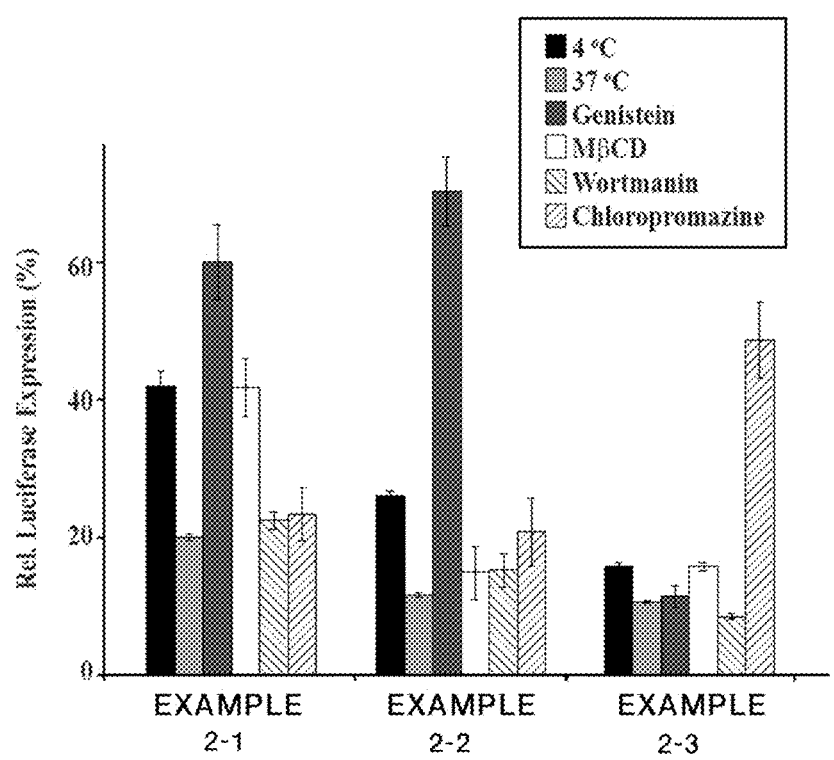

FIG. 7 is a graph illustrating a result of treatment with an endocytosis inhibitor agent for the identification of a cell delivery mechanism of the Zn-DPA complex compound.

Since the Zn-DPA complex compound synthesized in Example 2-1 depends on genistin and methyl-β-cyclodextrin (MβCD) without being affected by chloropromazine, it can be seen that the Zn-DPA complex compound delivers siRNA through clathrin-dependent caveolae-mediated endocytosis. Since the Zn-DPA complex compound synthesized in Example 2-2 depends only on genistin, it can be seen that the Zn-DPA complex compound delivers siRNA through clathrin-dependent and caveolin-dependent endocytosis. Further, since the Zn-DPA complex compound synthesized in Example 2-3 depends on chloropromazine, it can be seen that together with the result in FIG. 7, the Zn-DPA complex delivers siRNA through receptor-mediated endocytosis.

It should be understood that the appended drawings are not necessarily to scale, presenting a somewhat simplified representation of various preferred features illustrative of the basic principles of the invention. The specific design features of the present invention as disclosed herein, including, for example, specific dimensions, orientations, locations, and shapes will be determined in part by the particular intended application and use environment.

In the figures, reference numbers refer to the same or equivalent parts of the present invention throughout the several figures of the drawing.

DETAILED DESCRIPTION

Hereinafter reference will now be made in detail to various embodiments of the present invention, examples of which are illustrated in the accompanying drawings and described below. While the invention will be described in conjunction with exemplary embodiments, it will be understood that present description is not intended to limit the invention to those exemplary embodiments. On the contrary, the invention is intended to cover not only the exemplary embodiments, but also various alternatives, modifications, equivalents and other embodiments, which may be included within the spirit and scope of the invention as defined by the appended claims.

The present invention as described above will be described in more detail with reference to the following Examples, and the present invention is not limited thereto.

EXAMPLES

The following examples illustrate the invention and are not intended to limit the same.

Example 1. Synthesis of Dipicolylamine-Based Compound

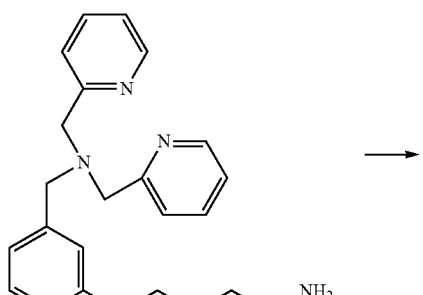

[Chemical Formula 3]

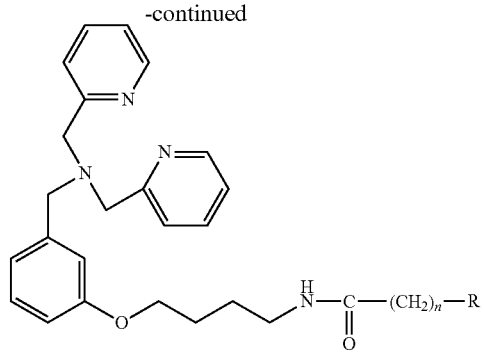

[Chemical Formula 1]

Example 1-1. Synthesis of Dipicolylamine-Based Compound Represented by Formula 1a

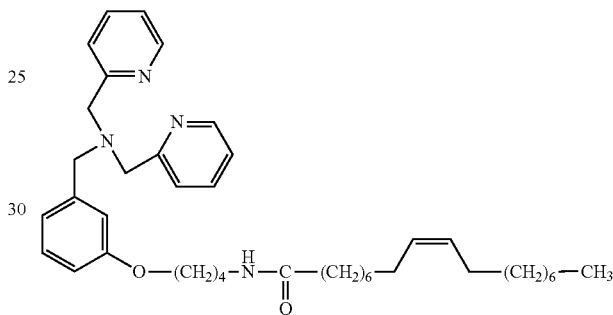

2-(4-(3-((bis(pyridin-2-yl)methyl)amino)methyl)phenoxy)butylamine) used as a raw material was synthesized according to a document (H. Jiang, B. D. Smith, *Chem. Commun.* 2006, 1407-1409).

2-(4-(3-((bis(pyridin-2-yl)methyl)amino)methyl)phenoxy)butylamine) (155 mg, 0.39 mmol) was dissolved in dichloromethane (10 mL). Oleic acid (140 μL, 0.43 mmol) and triethylamine (82 μL, 0.59 mmol) were added to a reaction solution, and then 1-[bis(dimethylamino)methylene]-1H-1,2,3-triazolo[4,5-b]pyridinium 3-oxide hexafluorophosphate (HATU; 226 mg, 0.59 mmol) was put thereinto, and the resulting mixture was stirred at room temperature for 16 hours. After completion of the reaction, the mixture solution was washed sequentially with an aqueous 0.5 M HCl solution (2×10 mL), a saturated aqueous NaHCO$_3$ solution (2×10 mL), and distilled water (1×10 mL), and then the organic layer was collected, dried by using anhydrous Na$_2$SO$_4$, and then distilled under reduced pressure. The obtained mixture was purified by using column chromatography (basic alumina; EtOAc) to obtain a target compound (105 mg) in the form of a yellow oil with a yield of 42%.

$^1$H NMR (400 MHz, CDCl$_3$) 8.51 (d, J=4 Hz, 2H), 7.66 (t, J=7.6 Hz, 2H), 7.60-7.58 (m, 2H), 7.21 (t, J=8 Hz, 1H), 7.13 (t, J=6 Hz, 2H), 7.00-6.96 (m, 2H), 6.75 (d, J=8 Hz, 1H), 5.80 (t, J=5.5 Hz, 1H), 5.35-5.31 (m, 2H), 3.97 (t, J=6 Hz, 2H), 3.81 (s, 4H), 3.66 (s, 2H), 3.32 (q, J=6.4 Hz, 2H), 2.13 (t, J=7.6 Hz, 2H), 2.00-1.99 (m, 4H), 1.81 (t, J=6.8 Hz, 2H), 1.69 (t, J=7.2 Hz, 2H), 1.59-1.64 (m, 2H), 1.28-1.26 (m, 20H), 0.87 (t, J=5.6 Hz, 3H); $^{13}$C NMR (100 MHz, CDCl$_3$) 173.1, 159.7, 158.9, 148.9, 140.5, 136.4, 129.9, 129.7, 129.3, 122.7, 121.9, 121.2, 115.0, 112.9, 67.3, 59.9, 58.4, 39.0, 36.89, 31.8, 29.8, 29.7, 29.5, 29.3, 29.2, 29.1, 27.2, 27.1, 26.6, 26.4, 25.8, 22.6, 14.1; HRMS (ESI⁺) calcd. for [M+Na]⁺ $C_{41}H_{60}N_4O_2Na^+$: m/z 663.4608. found: 663.4651.

Example 1-2. Synthesis of Dipicolylamine-Based Compound Represented by Formula 1b

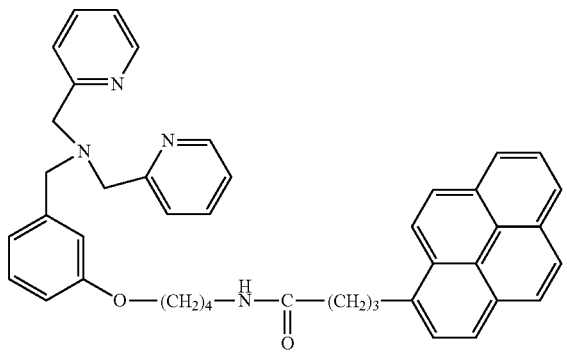

The target compound (159 mg) in the form of yellow oil was obtained with a yield of 63% by performing the same method as in Example 1-1 and using 1-pyrenebutyric acid (123 mg, 0.43 mmol) instead of oleic acid.

¹H NMR (300 MHz, CDCl₃) 8.46 (d, J=4.2 Hz, 2H), 8.23-8.20 (m, 1H), 8.11-8.08 (m, 2H), 8.07-8.00 (m, 2H), 7.95-7.92 (m, 3H), 7.78-7.76 (m, 1H), 7.57-7.51 (m, 4H), 7.17 (t, J=7.8 Hz, 1H), 7.06-7.02 (m, 2H), 6.96-6.92 (m, 2H), 6.69 (dd, J=8.1, 1.5 Hz, 1H), 5.76 (t, J=6.0 Hz, 1H), 3.88 (t, J=6.0 Hz, 2H), 3.76 (s, 4H), 3.61 (s, 2H), 3.32-3.23 (m, 4H), 2.17-2.12 (m, 4H), 1.74-1.68 (m, 2H), 1.63-1.56 (m, 2H); ¹³C NMR (75 MHz, CDCl₃) 172.6, 159.7, 158.9, 148.9, 140.6, 136.4, 135.9, 131.4, 130.9, 129.9, 129.3, 128.7, 127.4, 127.3, 126.7, 125.8, 125.0, 124.9, 124.9, 124.7, 123.3, 122.7, 121.9, 121.2, 115.1, 113.0, 67.3, 60.0, 58.4, 39.1, 36.0, 32.7, 27.4, 26.7, 26.4; HRMS (ESI⁺) calcd. for [M+Na]⁺ $C_{43}H_{42}N_4O_2Na^+$: m/z 669.3205. found: 669.3231.

Example 1-3. Synthesis of Dipicolylamine-Based Compound Represented by Formula 1c

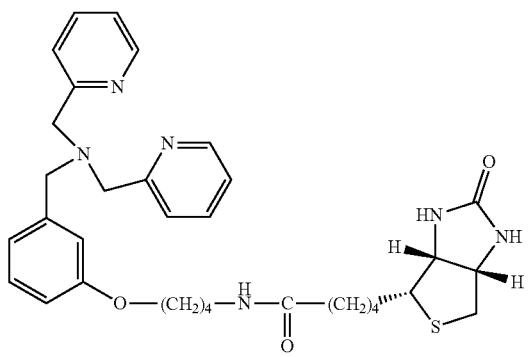

The target compound (52 mg) in the form of yellow oil was obtained with a yield of 25% by performing the same method as in Example 1-1 and using biotin (94 mg, 0.38 mmol) instead of oleic acid.

¹H NMR (300 MHz, CDCl₃) 8.48 (d, J=4.8 Hz, 2H), 7.64 (td, J=7.6, 1.6 Hz, 2H), 7.56-7.54 (m, 2H), 7.18 (t, J=7.8 Hz, 1H), 7.11 (t, J=6.2 Hz, 2H), 6.97-6.92 (m, 2H), 6.72 (dd, J=8.1, 1.5 Hz, 1H), 6.37 (s, 1H), 6.24 (t, J=5.5 Hz, 1H), 5.50 (s, 1H), 4.44-4.39 (m, 1H), 4.26-4.22 (m, 1H), 3.94 (t, J=6.1 Hz, 2H), 3.77 (s, 4H), 3.63 (s, 2H), 3.27 (q, J=6.4 Hz, 2H), 2.85-2.79 (m, 1H), 2.67-2.62 (m, 1H), 2.15 (t, J=7.3 Hz, 2H), 1.80-1.73 (m, 2H), 1.67-1.61 (m, 6H), 1.42-1.35 (m, 2H); ¹³C NMR (100 MHz, CDCl₃) 173.1, 163.8, 159.6, 158.9, 148.9, 140.5, 136.4, 129.3, 122.8, 122.0, 121.2, 115.1, 113.0, 67.4, 61.7, 60.1, 59.9, 58.4, 55.5, 40.5, 39.1, 36.0, 28.1, 28.0, 26.7, 26.3, 25.6; HRMS (ESI⁺) calcd. for [M+Na]⁺ $C_{33}H_{42}N_6O_3SNa^+$: m/z 625.2937. found: 625.2937.

Example 2. Synthesis of Zn-DPA Complex Compound

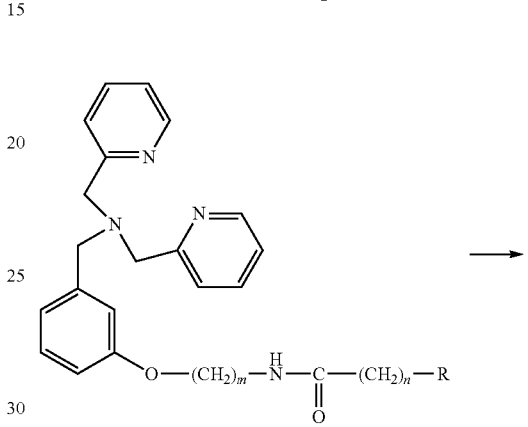

[Chemical Formula 1]

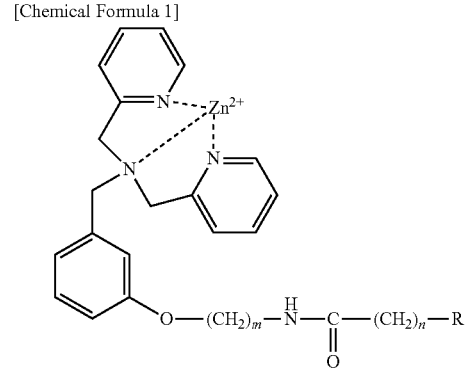

[Chemical Formula 2]

Example 2-1: Clathrin-Independent and Caveolae-Mediated Endocytosis in Lipid Raft Domains

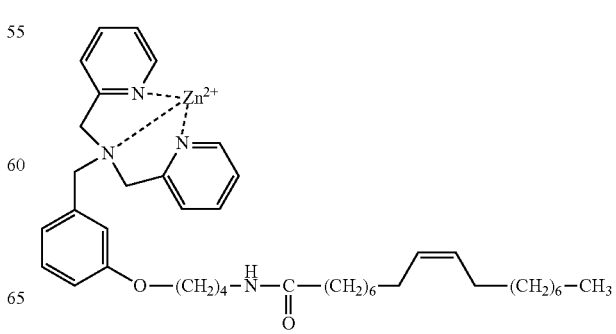

The dipicolylamine-based compound (41 mg, 0.064 mmol) synthesized in Example 1-1 was dissolved in methanol (5 mL), and then zinc nitrate hexahydrate (19 mg, 0.064 mmol) was added thereto, and the resulting mixture was stirred for 30 minutes. After the reaction solution was distilled under reduced pressure and the undissolved solid was filtered by adding dichloromethyl (2 mL) thereto, the filtrate was distilled under reduced pressure, and then dried in a vacuum state to obtain a white solid target compound (50 mg) with a yield of 94%.

$^1$H NMR (300 MHz, CDCl$_3$) 8.83 (d, J=5.1 Hz, 2H), 8.03 (t, J=7.5 Hz, 2H), 7.55 (t, J=6 Hz, 2H), 7.49 (d, J=7.8 Hz, 2H), 7.27 (t, J=6.6 Hz, 1H), 6.90 (d, J=7.5 Hz, 1H), 6.64-6.61 (m, 2H), 6.03 (t, J=6.3 Hz, 1H), 5.37-5.33 (m, 2H), 4.38-4.33 (m, 2H), 4.02-3.96 (m, 4H), 3.66 (d, 2H), 3.37-3.35 (m, 2H), 2.21 (t, J=7.2 Hz, 2H), 2.18-2.02 (m, 4H), 1.84-1.82 (m, 2H), 1.75-1.63 (m, 4H), 1.30-1.28 (m, 21H), 0.89 (t, J=6 Hz, 3H); $^{13}$C NMR (75 MHz, CDCl$_3$) 176.7, 159.3, 154.1, 149.1, 1403.9, 132.1, 130.0, 129.7, 125.2, 124.2, 123.4, 117.7, 114.6, 67.5, 55.4, 55.0, 39.0, 36.7, 31.8, 29.7, 29.7, 29.5, 29.3, 29.2, 29.1, 27.2, 27.1, 26.4, 26.3, 25.8, 22.6; HRMS (ESI$^+$) calcd. for [M+NO$_3$]$^+$ C$_{41}$H$_{60}$N$_5$O$_5$Zn$^+$: m/z 766.3880. found: 766.3901.

Example 2-2: Clathrin and Caveolin-Independent Endocytosis

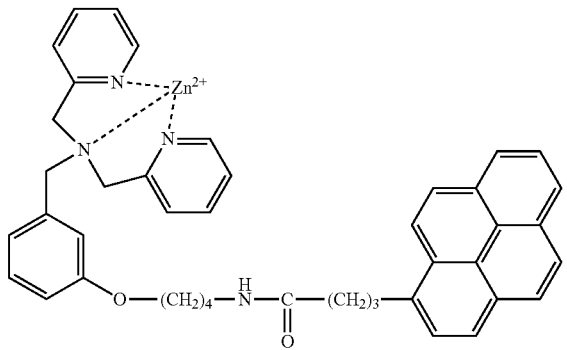

The Zn-DPA complex compound was prepared by performing the method in Example 2-1, and a white solid target compound (12 mg) was obtained with a yield of 96% by using the dipicolylamine-based compound (11 mg, 0.017 mmol) synthesized in Example 1-2 as a reaction material.

$^1$H NMR (300 MHz, CDCl$_3$) 8.82 (d, J=4.8 Hz, 2H), 8.31-8.28 (m, 1H), 8.18-8.07 (m, 4H), 8.04-8.02 (m, 3H), 7.90-7.85 (m, 3H), 7.44 (t, J=6.3 Hz, 2H), 7.34-7.24 (m, 3H), 6.89-6.87 (m, 1H), 6.56-6.54 (m, 2H), 5.83 (t, J=5.4 Hz 1H), 4.26-4.20 (m, 2H), 3.96 (t, J=6 Hz, 2H), 3.91-3.86 (m, 2H), 3.58 (s, 2H), 3.42-3.34 (m, 4H), 2.36-2.32 (m, 2H), 2.27-2.20 (m, 2H), 1.86-1.80 (m, 2H), 1.76-1.69 (m, 2H); $^{13}$C NMR (75 MHz, CDCl$_3$) 172.9, 159.3, 153.8, 149.1, 140.6, 135.9, 132.0, 131.4, 130.8, 129.9, 129.8, 128.7, 127.4, 127.3, 127.3, 126.7, 125.9, 125.1, 124.9, 124.7, 123.9, 123.4, 123.3, 117.7, 114.4, 67.4, 55.3, 54.8, 53.4, 38.9, 36.1, 32.7, 27.6, 26.4; HRMS (ESI$^+$) calcd. for [M-H]$^+$ C$_{43}$H$_{41}$N$_4$O$_2$Zn$^+$: m/z 709.2510. found: 709.2526; calcd. for [M+NO$_3$]$^+$ C$_{43}$H$_{42}$N$_5$O$_5$Zn$^+$ m/z. 772.2472. found: 772.2485.

Example 2-3: Receptor-Mediated Endocytosis

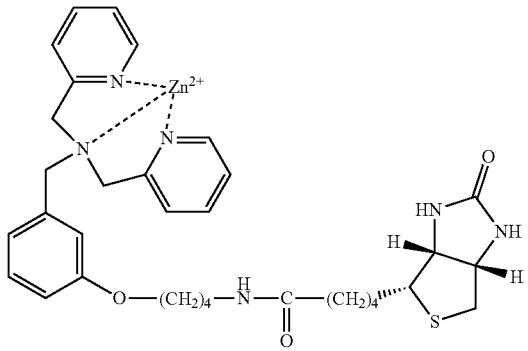

The Zn-DPA complex compound was prepared by performing the method in Example 2-1, and a white solid target compound (38 mg) was obtained with a yield of 79% by using the dipicolylamine-based compound (40 mg, 0.066 mmol) synthesized in Example 1-3 as a reaction material.

$^1$H NMR (400 MHz, CDCl$_3$) 8.66 (s, 2H), 8.06 (t, J=7.6 Hz, 2H), 7.60 (t, J=6.0 Hz, 2H), 7.54-7.52 (m, 2H), 7.20 (t, J=7.7 Hz, 1H), 6.81 (dd, J=1.8, 8.2 Hz, 1H), 6.76-6.71 (m, 2H), 4.45-4.42 (m, 1H), 4.31-4.25 (m, 3H), 3.93-3.87 (m, 4H), 3.71 (s, 2H), 3.19 (t, J=6.8 Hz, 2H), 3.15-3.10 (m, 1H), 2.84-2.80 (m, 1H), 2.60-2.57 (m, 1H), 2.12 (t, J=7.2 Hz, 2H), 1.74-1.71 (m, 2H), 1.64-1.61 (m, 4H), 1.55-1.53 (m, 2H), 1.34-1.33 (m, 2H); $^{13}$C NMR (75 MHz, CDCl$_3$) 174.7, 165.2, 164.8, 159.2, 155.0, 148.2, 141.4, 134.8, 132.9, 129.6, 124.9, 124.9, 123.4, 123.3, 117.1, 114.9, 67.3, 62.2, 60.5, 56.8, 55.7, 55.7, 55.5, 39.6, 38.6, 35.5, 28.3, 28.0, 26.2, 25.7, 25.5; HRMS (ESI$^+$) calcd. for [M-H]$^+$ C$_{33}$H$_{41}$N$_6$O$_3$SZn$^+$: m/z 665.2241. found: 665.2263.

Example 2-4. Synthesis of Zn-BzDPA Complex Compound Represented by Formula 2d

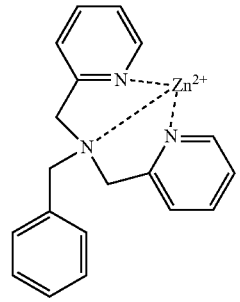

The Zn-DPA complex compound was prepared by performing the method in Example 2-1, a white precipitate obtained during the reaction by using N-benzyl(pyridin-2-yl)-N-((pyridin-2-yl)methyl)methaneamine (110 mg, 0.38 mmol) as a reaction material was washed several times with diethyl ether, and then a white solid target compound (106 mg) was obtained with a yield of 62%. In this case, N-benzyl (pyridin-2-yl)-N-((pyridin-2-yl)methyl)methaneamine as a reaction material was synthesized and used by a document (*Inorg. Biochem.* 2015, 153, 143-149.).

$^1$H NMR (300 MHz, DMSO) 8.67 (d, J=6.4 Hz, 2H), 8.11 (t, J=10.2 Hz, 2H), 7.67-7.62 (m, 4H), 7.50-7.48 (m, 3H), 7.39-7.37 (m, 2H), 4.27 (d, J=21.2 Hz, 2H), 3.75 (s, 2H), 3.71 (d, J=16.0 Hz, 2H); $^{13}$C NMR (75 MHz, DMSO) 154.6, 148.3, 141.2, 132.1, 132.0, 129.1, 125.3, 125.2, 57.0, 55.8; HRMS (FAB$^+$) calcd. for [M+NO$_3$]$^+$ C$_{19}$H$_{19}$N$_4$O$_3$Zn$^+$: m/z 415.0746. found: 415.0749.

Example 2-5. Synthesis of Zn-BzDPA Complex Compound Represented by Formula 2e

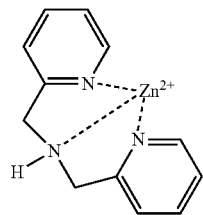

The Zn-DPA complex compound was prepared by performing the method in Example 2-1, a white precipitate obtained during the reaction by using 2,2'-dipicolylamine (100 mg, 0.50 mmol) as a reaction material was washed several times with diethyl ether, and then a white solid target compound (126 mg) was obtained with a yield of 70%.

$^1$H NMR (400 MHz, DMSO) 8.56 (d, J=4.0 Hz, 2H), 7.98 (td, J=7.6, 1.2 Hz, 2H), 7.51-7.49 (m, 4H), 5.15 (s, 1H), 4.45 (dd, J=16.6, 6.6 Hz, 2H), 3.92 (d, J=16.6 Hz, 2H); $^{13}$C NMR (100 MHz, DMSO) 155.8, 147.3, 140.3, 124.6, 124.1, 52.7; HRMS (FAB$^+$) calcd. for [M+NO$_3$]$^+$ C$_{12}$H$_{13}$N$_4$O$_3$Zn$^+$: m/z 325.0276. found: 325.0279.

TEST EXAMPLES

Test Example 1. Determination of siRNA Delivery Efficiency (1) Preparation of Composite of siRNA and Zn-DPA Complex Compound An siRNA solution (Solution A) at a concentration of 5 μM was prepared by dissolving siRNA in water. A complex compound solution (Solution B) was prepared by dissolving the Zn-DPA complex compound in dimethyl sulfoxide (DMSO) in a separate container. The solution of the complex compound solution was determined according to the molar ratio of siRNA and the Zn-DPA complex compound. Solution A and Solution B prepared above were mixed at a volume ratio of 1:2, and the resulting mixture was left to stand at room temperature for 10 minutes, and then used.

(2) Evaluation of Stability of Hydrolase Against Composite of siRNA and Zn-DPA Complex Compound Two composites each having a molar ratio of siRNA and the Zn-DPA complex compound of 1:0, 1:16, 1:31, 1:63, 1:125, 1:250, 1:500, and 1:1,000 were prepared according to Experimental Example 1 (1).

In the two composites, a buffer solution (Tris-HCl 10 mM, NaCl 100 mM, pH 7.2) was added to the one composite, and RNase A (0.1 Unit) dissolved in the same buffer solution was added to the other composite. For each sample, a constant-temperature treatment was performed at 37° C. for 30 minutes, and then RNA was extracted by a general phenol extraction method. A loading dye was added to the extract, and the amount of remaining RNA was measured by using a 1.0% agarose gel.

FIG. 2 illustrates a result in which the Zn-DPA complex compounds synthesized in Examples 2-1, 2-2, and 2-3 are each treated with RNase A hydrolase, and then the mobility of siRNA is specified. According to FIG. 2, it was confirmed that the Zn-DPA complex compound synthesized in Example 2-1 had the best stability against the hydrolase, and it could be confirmed that up until a molar ratio of 1:63 to 1,000, a group treated with the hydrolase and a non-treatment group equally preserved RNA.

Test Example 2. Evaluation of Particle Size of Composite of siRNA and Zn-DPA Complex Compound Composites having a molar ratio of siRNA and the Zn-DPA complex compound of 1:100, 1:400, and 1:1,000 were prepared according to Experimental Example 1 (1), and the composites were diluted with distilled water such that the Zn-DPA complex compound had a final concentration of 5 μM and a final volume of 1 mL. The Zn-DPA complex compound was dissolved in DMSO at a concentration of 10 mM, and then the resulting solution was diluted with distilled water, such that the Zn-DPA complex compound had a final concentration of 5 μM and a final volume of 1 mL. The particle size of the solution prepared above was measured by using a particle size distribution analyzer (Zetasizer ZS, Malvern, UK) which uses dynamic light scattering.

FIG. 3 illustrates a result of measuring the particle sizes of the composite of siRNA and the Zn-DPA complex compound. According to FIG. 3, the composites of siRNA and the Zn-DPA complex compound had a particle size of about 100 nm, and all the composites exhibited a size of 200 nm or less, which is appropriate for the composites to pass through a cell membrane by endocytosis.

Test Example 3. Evaluation of In Vitro Toxicity for Zn-DPA Complex Compound

In order to evaluate the toxicity of the Zn-DPA complex compounds synthesized in Examples 1-1, 1-2, 1-3, 1-4, and 1-5, the following experiments were performed.

According to Experimental Example 1 (1), composites having a molar ratio of siRNA (luciferase siRNA, siLuc) and the Zn-DPA complex compound of 1:50, 1:100, 1:200, 1:400, 1:600, 1:800, and 1:1,000 were prepared, and the samples were treated with HeLa, HepG2, and HCT116 cell lines in a serum-free medium by making the concentration of siLuc per sample constant at 20 nM. After 4 hours, the medium was exchanged with a 10% serum medium, and then the samples were cultivated for hours. According to a general method using 3-(4,5-dimethylthiazol-2-yl)-2,5-diphenyltetrazolium bromide (MTT), living cells were stained, and the absorbance at 570 nm was measured by using a microplate fluorescence analyzer (MSF; Victor3 V Multi-label Counter, PerkinElmer, Wellesley, Mass.). The results are illustrated in FIG. 4.

According to FIG. 4, the composites having a molar ratio of siRNA and the Zn-DPA complex compound of 1:50 to 1:1,000 were less toxic than Lipofecamine™, which is a commercially available cell permeation auxiliary agent. Accordingly, it can be seen that the Zn-DPA complex compound is a novel material which secures toxicity stability as an siRNA receptor.

Test Example 4. Evaluation (1) of siRNA Delivery Efficiency for Zn-DPA Complex Compound In order to evaluate the delivery efficiency of siRNA (luciferase siRNA, siLuc) for the Zn-DPA complex compounds synthesized in Examples 1-1, 1-2, 1-4, and 1-5, cell experiments are performed as follows.

According to Experimental Example 1 (1), composites having a molar ratio of siRNA (luciferase siRNA, siLuc) and the Zn-DPA complex compound of 1:50, 1:100, 1:200, 1:400, 1:600, 1:800, and 1:1,000 were prepared, and the concentration of siLuc per sample was adjusted constantly at 20 nM. The composite was treated with ssPEI/CMV-LUC (1 μg) in HeLa, HepG2, and HCT116 cell lines, and was washed with a Dulbecco's phosphate buffered saline solution (DPBS) after 6 hours, and then the composite was treated in a serum-free medium. After 4 hours, the medium was exchanged with a 10% serum medium, and then the samples were cultivated at 37° C. for 24 hours. The cells were washed with the DPBS and were dissolved in a lysis buffer (200 μL), and then the degree of expression of the luciferase was determined by using a microplate fluorescence analyzer (VICTOR 3 V Multilabel Counter, PerkinElmer, Wellesley, Mass.). The results are illustrated in FIG. 5.

According to FIG. 5, judging from the fact that the expression of luciferase is reduced, it can be confirmed that the Zn-DPA complex compound in Example 2-4 or 2-5, in which only the phosphate-directing functional part of Zn-DPA is present, has an siRNA delivery efficiency. It could be confirmed that the Zn-DPA complex compound in Example 2-1 or 2-2 had significantly improved siRNA delivery efficiency as compared to the Zn-DPA complex compound in Example 2-4 or 2-5. That is, it can be seen that the cell membrane-directing functional part is linked to the phosphate-directing functional part of Zn-DPA, and as a result, the siRNA delivery efficiency is significantly improved. In particular, it could be confirmed that the Zn-DPA complex compound synthesized in Example 2-2 had a better efficiency than Lipofecamine™, which is a commercially available cell permeation auxiliary agent when the molar ratio of siRNA:the Zn-DPA complex compound was 1:400.

Test Example 5. Evaluation (2) of siRNA Delivery Efficiency for Zn-DPA Complex Compound In order to evaluate the delivery efficiency of siRNA (luciferase siRNA, siLuc) for the Zn-DPA complex compound synthesized in Example 1-3, a cell experiment was performed in the same manner as in Experimental Example 4 by classifying the experimental groups into groups treated with biotin at a concentration of 0.5 mM and 5 mM 30 minutes before treating the groups with a composite of siRNA and the Zn-DPA complex compound, or a non-treatment group. However, as the cell line, HepG2 and HCT116 were used, and the molar ratio of siRNA:the Zn-DPA complex compound was fixed at 1:400. The results are illustrated in FIG. 6.

According to FIG. 6, in the HepG2 cell line including a large amount of a biotin transporter, the amount of luciferase expressed significantly varied depending on the presence or absence of biotin, whereas in the HCT116 cell line, a change in amount of luciferase expressed was slight regardless of the presence or absence of treatment with biotin. That is, it could be seen that in the case of the Zn-DPA complex compound synthesized in Example 1-3, a biotin receptor was profoundly involved in the siRNA delivery.

Example 8. Studies on Delivery Mechanism of siRNA Transporter Through Cell Experiment In order to observe the delivery mechanism for siRNA (luciferase siRNA (siLuc) of each transporter, inhibitory agents for the different endocytosis routes were treated 1 hour before the composite of siRNA and the Zn-DPA complex compound was treated. A cell experiment was performed in the same manner as in Experimental Example 4 by treating each of 300 μM of genistein, 5 mg/mL of MβCD, 200 nM of wortmanin, and 2.5 μg/mL of chlorpromazine as the inhibitory agent. However, as the cell line, HepG2 was used, and the molar ratio of siRNA:the Zn-DPA complex compound was fixed at 1:400. Further, in order to inhibit the energy-dependent endocytosis, the experiment was performed in the same manner as in Experimental Example 4, and the experiment was performed by cultivating cells at 4° C. The results are illustrated in FIG. 7.

It could be confirmed that the delivery mechanism varied depending on the type of cell membrane-directing functional part. It can be seen that the Zn-DPA complex compound synthesized in Example 2-1 delivers siRNA to cells through a delivery mechanism by means of a clathrin-independent and caveolae-mediated endocytosis. It can be seen that the Zn-DPA complex compound synthesized in Example 2-2 delivers siRNA to cells through a delivery mechanism by means of a clathrin-independent and caveolin-independent endocytosis. It can be seen that the Zn-DPA complex compound synthesized in Example 2-3 delivers siRNA to cells through a delivery mechanism by means of a receptor-mediated endocytosis.

The invention has been described in detail with reference to preferred embodiments thereof. However, it will be appreciated by those skilled in the art that changes may be made in these embodiments without departing from the principles and spirit of the invention, the scope of which is defined in the appended claims and their equivalents.

What is claimed is:

1. A dipicolylamine-based compound represented by the following Formula 1:

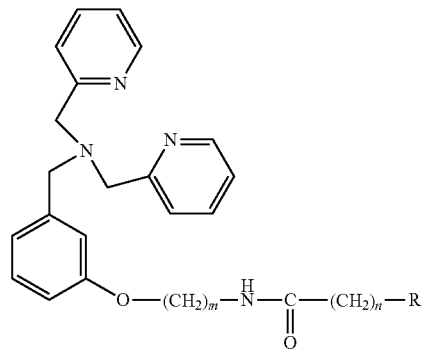

[Formula 1]

wherein R represents a saturated or unsaturated linear aliphatic hydrocarbon group having 5 to 15 carbon atoms; an aromatic hydrocarbon group having 6 to 16 carbon atoms; or a monocyclic or fused cyclic aliphatic heterocyclic group including 1 to 5 heteroatoms selected from the group of a nitrogen atom (N), a sulfur atom (S) and an oxygen atom (O), wherein the aliphatic heterocyclic group optionally includes an oxo (=O) group, and m represents an integer from 1 to 10, and n represents an integer from 0 to 10.

2. The dipicolylamine-based compound of claim 1, wherein R represents a linear aliphatic hydrocarbon group having 2 to 10 carbon atoms and including 0 to 3 double bonds;

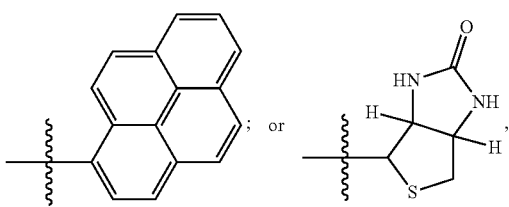 [SMILES: *c1ccc2ccc3cccc4ccc1c2c34 ; *C1SCC2NC(=O)NC21]

and m and n are each an integer from 3 to 8.

3. The dipicolylamine-based compound of claim 1, wherein the dipicolylamine-based compound is represented by the following Formula 1a, 1b, or 1c:

[Formula 1a]

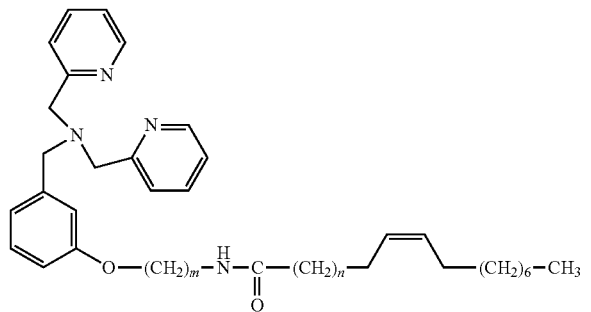

[Formula 1b]

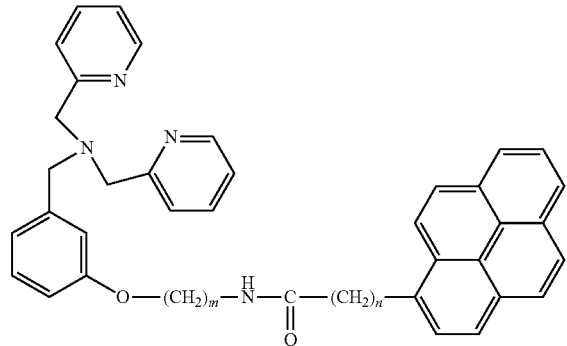

[Formula 1c]

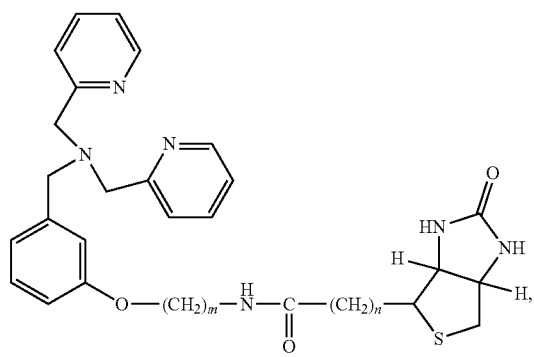

wherein m represents an integer from 1 to 10, and n represents an integer from 0 to 10.

4. A Zn-DPA complex compound represented by the following Formula 2:

[Formula 2]

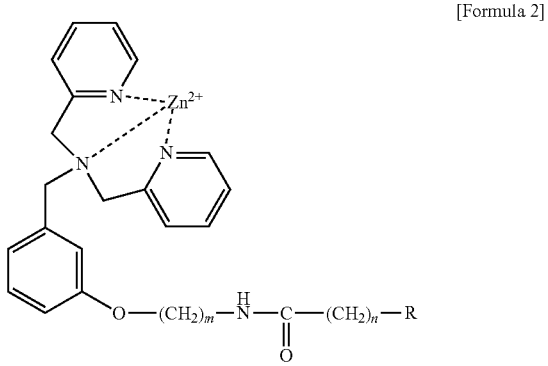

wherein R represents a saturated or unsaturated linear aliphatic hydrocarbon group having 2 to 10 carbon atoms; a monocyclic or fused-cyclic aromatic hydrocarbon group having 6 to 16 carbon atoms; or a monocyclic or fused-cyclic aliphatic heterocyclic group comprising 1 to 5 heteroatoms composed of a nitrogen atom (N), a sulfur atom (S), and an oxygen atom (O), and m represents an integer from 1 to 10 and n represents an integer from 0 to 10.

5. The Zn-DPA complex compound of claim 4, wherein the Zn-DPA complex compound is represented by the following Formula 2a, 2b, or 2c:

[Formula 2a]

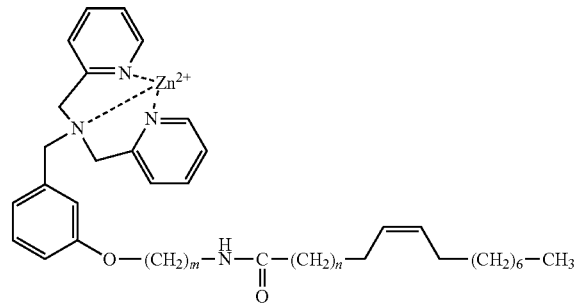

[Formula 2b]

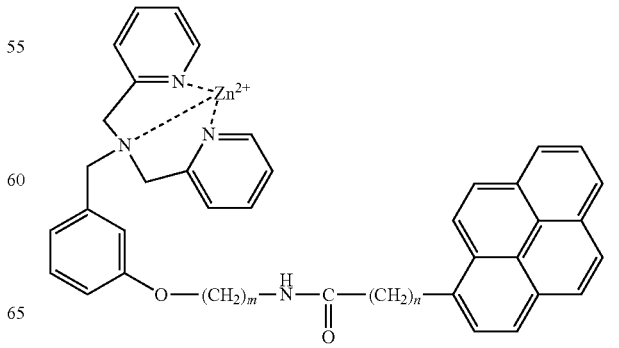

-continued

[Formula 2c]

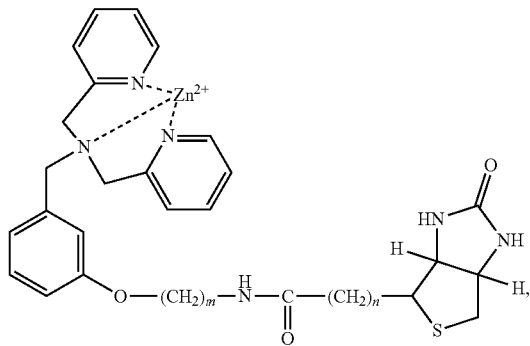

wherein m represents an integer from 1 to 10, and n represents an integer from 0 to 10.

6. An siRNA transporter represented by the following Formula 2:

[Formula 2]

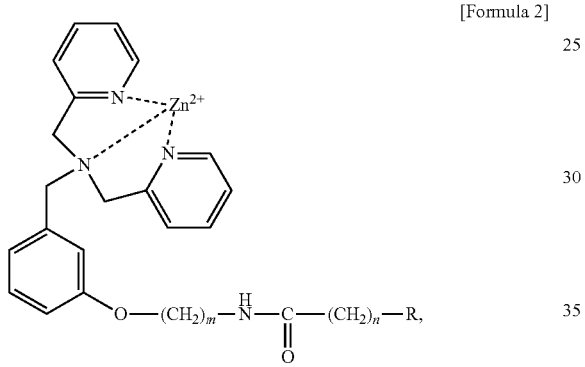

wherein R represents a saturated or unsaturated linear aliphatic hydrocarbon group having 2 to 10 carbon atoms; a monocyclic or fused-cyclic aromatic hydrocarbon group having 6 to 16 carbon atoms; or a monocyclic or fused-cyclic aliphatic heterocyclic group comprising 1 to 5 heteroatoms composed of a nitrogen atom (N), a sulfur atom (S), and an oxygen atom (O), and m represents an integer from 1 to 10 and n represents an integer from 0 to 10.

7. The siRNA transporter of claim 6, wherein the siRNA transporter is represented by the following Formula 2a, 2b, or 2c:

[Formula 2a]

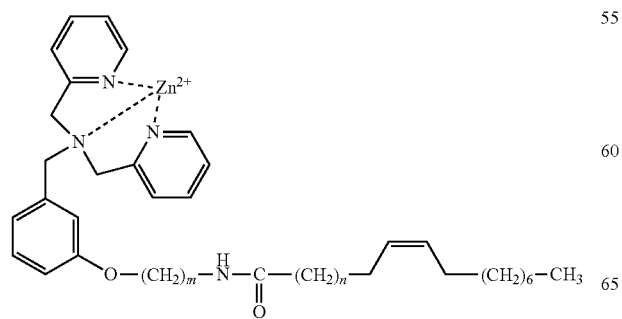

-continued

[Formula 2b]

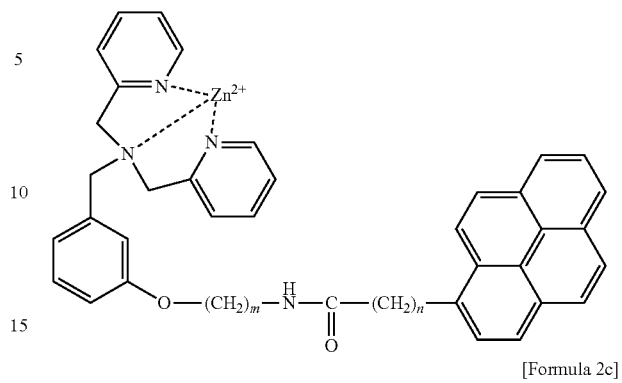

[Formula 2c]

wherein m represents an integer from 1 to 10, and n represents an integer from 0 to 10.

8. An siRNA delivery system comprising:
siRNA; and
an siRNA transporter represented by the following Formula 2:

[Formula 2]

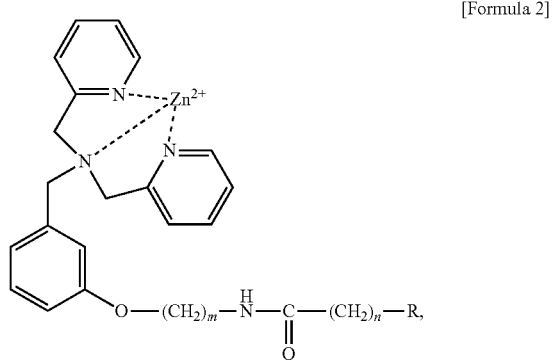

wherein R represents a saturated or unsaturated linear aliphatic hydrocarbon group having 2 to 10 carbon atoms; a monocyclic or fused-cyclic aromatic hydrocarbon group having 6 to 16 carbon atoms; or a monocyclic or fused-cyclic aliphatic heterocyclic group comprising 1 to 5 heteroatoms composed of a nitrogen atom (N), a sulfur atom (S), and an oxygen atom (O), and m represents an integer from 1 to 10 and n represents an integer from 0 to 10.

9. The siRNA delivery system of claim 8, wherein the siRNA transporter is a Zn-DPA complex compound represented by the following Formula 2a, 2b, or 2c:

[Formula 2a]

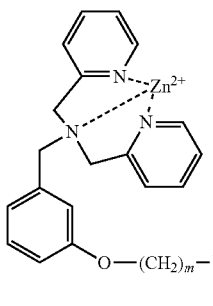

[Formula 2b]

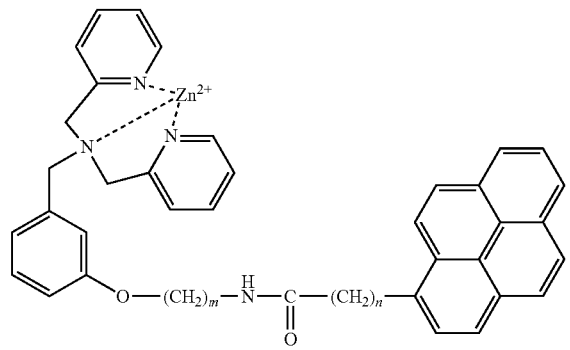

[Formula 2c]

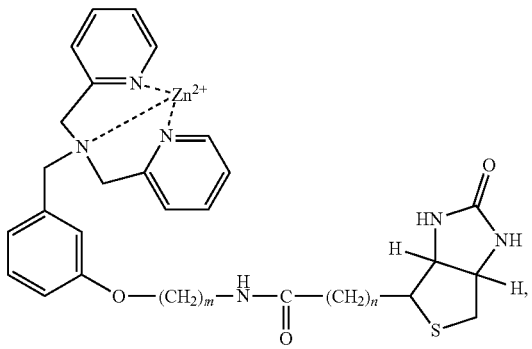

wherein m represents an integer from 1 to 10, and n represents an integer from 0 to 10.

10. The siRNA delivery system of claim 8, wherein a molar ratio of siRNA and the siRNA transporter is 1:16 to 1,000.

11. The siRNA delivery system of claim 10, wherein a molar ratio of siRNA and the siRNA transporter is 1:100 to 600.

* * * * *